(12) United States Patent
Zikorus et al.

(10) Patent No.: US 7,789,876 B2
(45) Date of Patent: Sep. 7, 2010

(54) METHOD AND APPARATUS FOR POSITIONING A CATHETER RELATIVE TO AN ANATOMICAL JUNCTION

(75) Inventors: Arthur W. Zikorus, San Jose, CA (US); Ralph G. DePalma, Walnut Creek, CA (US); Christopher S. Jones, Sunnyvale, CA (US); Brian E. Farley, Los Altos, CA (US); James G. Chandler, Boulder, CO (US)

(73) Assignee: Tyco Healthcare Group, LP, Mansfield, MA (US)

( * ) Notice: Subject to any disclaimer, the term of this patent is extended or adjusted under 35 U.S.C. 154(b) by 1753 days.

(21) Appl. No.: 09/825,741

(22) Filed: Apr. 3, 2001

(65) Prior Publication Data

US 2002/0068866 A1     Jun. 6, 2002

(51) Int. Cl.
*A61B 18/18* (2006.01)
(52) U.S. Cl. .............................. 606/41; 606/27; 606/28; 606/29; 606/30; 606/31; 606/32; 606/42; 600/407; 600/473; 600/476; 600/478; 604/22
(58) Field of Classification Search .................. 600/424, 600/373, 435, 487, 374, 462, 585, 437, 459, 600/461, 439, 407, 473, 476, 478, 479; 606/167, 606/159, 200, 153, 27–32, 41, 42; 604/164.12, 604/22
See application file for complete search history.

(56) References Cited

U.S. PATENT DOCUMENTS 4,862,887 A     9/1989   Weber et al.

(Continued)

FOREIGN PATENT DOCUMENTS

EP     1527748 A     5/2005

(Continued)

OTHER PUBLICATIONS

BioNavigation System From NAVION.

(Continued)

*Primary Examiner*—Brian Casler
*Assistant Examiner*—Baisakhi Roy
(74) *Attorney, Agent, or Firm*—Knobbe, Martens, Olson & Bear, LLP

(57) ABSTRACT

An electrode catheter is introduced into a vein or other hollow anatomical structure, and is positioned at a treatment site within the structure. The end of the catheter is positioned near a junction formed in the structure. This junction can be the sapheno-femoral junction. The position of the catheter near the junction is determined based on a signal from a device associated with the catheter within the structure. A fiber optic filament which emits light is used with the catheter or a guide wire over which the catheter is advanced. The light is visible externally from the patient. The light dims and may no longer externally visible at the sapheno-femoral junction where the catheter moves past the deep fascia and toward the deep venous system. The position of the catheter can be determined based on this external observation. The position of the catheter can also be determined based on measured parameters such as temperature or flow rate within the structure, and the measured changes in one or more of these parameters as the catheter nears the junction. The hollow anatomical structure can be compressed for this procedure. The position of the catheter can also be determined mechanically by including a hook-shaped tip on the catheter or guide wire which would physically engage the junction.

39 Claims, 5 Drawing Sheets

U.S. PATENT DOCUMENTS

| | | | |
|---|---|---|---|
| 5,022,399 A * | 6/1991 | Biegeleisen | 600/468 |
| 5,042,486 A | 8/1991 | Pfeiler et al. | |
| 5,282,484 A * | 2/1994 | Reger | 128/898 |
| 5,425,367 A | 6/1995 | Shapiro et al. | |
| 5,441,516 A | 8/1995 | Wang et al. | |
| 5,531,739 A | 7/1996 | Trelles | |
| 5,556,396 A * | 9/1996 | Cohen et al. | 606/42 |
| 5,584,830 A | 12/1996 | Ladd et al. | |
| 5,588,432 A | 12/1996 | Crowley | |
| 5,601,580 A * | 2/1997 | Goldberg et al. | 606/159 |
| 5,617,854 A | 4/1997 | Munsif | |
| 5,626,578 A | 5/1997 | Tihon | |
| 5,702,438 A | 12/1997 | Avitall | |
| 5,728,122 A * | 3/1998 | Leschinsky et al. | 606/213 |
| 5,740,808 A * | 4/1998 | Panescu et al. | 600/424 |
| 5,797,905 A | 8/1998 | Fleischman et al. | |
| 5,830,210 A * | 11/1998 | Rudko et al. | 606/15 |
| 5,830,224 A * | 11/1998 | Cohn et al. | 606/167 |
| 5,837,003 A | 11/1998 | Ginsburg | |
| 5,843,152 A | 12/1998 | Tu | |
| 5,902,254 A | 5/1999 | Magram | |
| 5,938,623 A | 8/1999 | Quiachon et al. | |
| 5,984,915 A | 11/1999 | Loeb | |
| 6,013,073 A | 1/2000 | Choukroun | |
| 6,120,516 A * | 9/2000 | Selmon et al. | 606/159 |
| 6,176,854 B1 | 1/2001 | Cone | |
| 6,183,468 B1 | 2/2001 | Swanson et al. | |
| 6,190,353 B1 * | 2/2001 | Makower et al. | 604/95.01 |
| 6,200,332 B1 | 3/2001 | Del Giglio | |
| 6,206,898 B1 * | 3/2001 | Honeycutt et al. | 606/159 |
| 6,235,024 B1 * | 5/2001 | Tu | 606/41 |
| 6,248,117 B1 * | 6/2001 | Blatter | 606/153 |
| 6,304,776 B1 | 10/2001 | Muntermann | |
| 6,322,559 B1 | 11/2001 | Daulton et al. | |
| 6,398,777 B1 * | 6/2002 | Navarro et al. | 606/7 |
| 6,400,980 B1 * | 6/2002 | Lemelson | 600/478 |
| 6,544,230 B1 * | 4/2003 | Flaherty et al. | 604/164.12 |
| 6,640,138 B1 | 10/2003 | Schaefermeyer | |
| 6,723,094 B1 * | 4/2004 | Desinger | 606/50 |
| 6,770,070 B1 * | 8/2004 | Balbierz | 606/41 |
| 7,406,970 B2 * | 8/2008 | Zikorus et al. | 128/898 |
| 2001/0041888 A1 | 11/2001 | Goldman et al. | |
| 2003/0078569 A1 | 4/2003 | Caldera | |
| 2003/0125759 A1 | 7/2003 | Mirizzi et al. | |
| 2003/0191460 A1 | 10/2003 | Hobbs | |
| 2004/0059397 A1 | 3/2004 | Sinofsky et al. | |
| 2004/0092913 A1 | 5/2004 | Hennings | |
| 2004/0122420 A1 | 6/2004 | Amoah | |
| 2004/0199151 A1 | 10/2004 | Neuberger | |
| 2004/0260333 A1 * | 12/2004 | Dubrul et al. | 606/200 |
| 2005/0015123 A1 | 1/2005 | Paithankar | |
| 2005/0107738 A1 * | 5/2005 | Slater et al. | 604/96.01 |
| 2005/0131400 A1 | 6/2005 | Hennings | |
| 2006/0142824 A1 | 6/2006 | Zikorus et al. | |
| 2007/0016272 A1 | 1/2007 | Thompson et al. | |
| 2007/0049999 A1 | 3/2007 | Esch | |
| 2007/0050000 A1 | 3/2007 | Esch et al. | |
| 2007/0055326 A1 | 3/2007 | Farley | |
| 2007/0055327 A1 | 3/2007 | Esch | |
| 2007/0100405 A1 | 5/2007 | Thompson et al. | |
| 2007/0179575 A1 | 8/2007 | Esch et al. | |

FOREIGN PATENT DOCUMENTS

| | | |
|---|---|---|
| WO | WO 93/08755 A | 5/1993 |
| WO | WO 98/55046 A | 12/1998 |
| WO | WO 99/11185 A | 3/1999 |
| WO | WO 00/10475 | 2/2000 |
| WO | WO 00/32129 | 8/2000 |
| WO | WO 2005/034783 A | 4/2005 |
| WO | WO 2006/069313 A | 6/2006 |

OTHER PUBLICATIONS

Starkhammar, et al, *Central Venous Catheter Placement Using Electromagnetic Position Sensing: A Clinical Evaluation*, Biomedical Instrumentation & Technology, pp. 164-170, Mar./Apr. 1996.

Boné Salat, Carlos; "Endoluminal Diode-Laser Treatment of Varicose Veins, Preliminary Study"; Patologia Vascular; Jan. 1999; pp. 32-39; vol. V; Spain.

Cohen, Monique S., et al.; "Ambulatory Phlebectomy Using The Tumescent Technique For Local Anesthesia"; Dermatol Surg; 1995;21:315-318; USA.

Hejhal, L., et al.; "Endovascular Electrocoagulation Of Superficial Varices Of The Lower Limbs"; Surgical Outlooks; XXXVIII—6—1959.

Puglisi, B., et al.; "Application Of The ND-YAG Laser In The Treatment Of Varicose Syndrome"; 1989; pp. 839-842; John Libbey Eurotext Ltd.

International Search Report for Application No. PCT-US2006-028454 mailed Mar. 28, 2007.

U.S. Appl. No. 11/491,065, filed Jul. 21, 2006, Esch.

U.S. Appl. No. 11/732,771, filed Apr. 4, 2007, Nguyen, et al.

Avitall et al, "The Effects of Electrode - Tissue Contact on Radiofrequency Lession Generation", Dec. 1997, PACE, vol. 20, 2899-2910.

Cao et al, "Using Electrical Impedance to Predict Catheter-Endocardial Contact During RF Cardiac Ablation", Mar. 2002, IEEE Transactions on Biomedical Engineering, vol. 49 No. 3, 247-252.

Zheng et al, "Electrode Impedance: An Indicator of Electrode - Tissue Contact and Lesion Dimensions During Linear Ablation", 2000, Journal of Interventional Cardiac Electrophysiology, 645-654.

International Search Report and Written Opinion of the International Searching Authority for International Application No. PCT/US2006/028454.

U.S. Appl. No. 11/313,512, filed Dec. 20, 2005, Zikorus et al.

U.S. Appl. No. 11/491,067, filed Jun. 21, 2006, Esch et al.

U.S. Appl. No. 11/491,346, filed Jul. 21, 2006, Farley.

U.S. Appl. No. 11/491,348, filed Jul. 21, 2006, Thompson et al.

U.S. Appl. No. 11/491,424, filed Jul. 21, 2006, Esch.

U.S. Appl. No. 11/236,316, filed Sep. 27, 2005, Thompson et al.

U.S. Appl. No. 11/490,638, filed Jul. 21, 2006, Esch.

\* cited by examiner

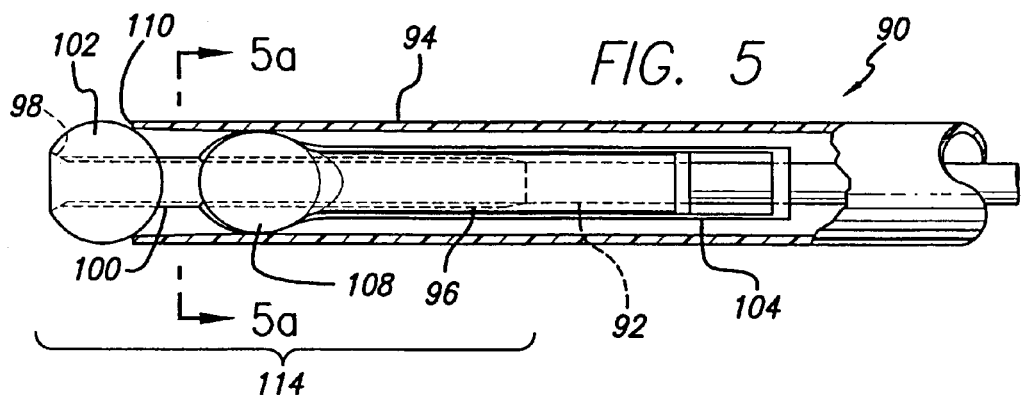
FIG. 5
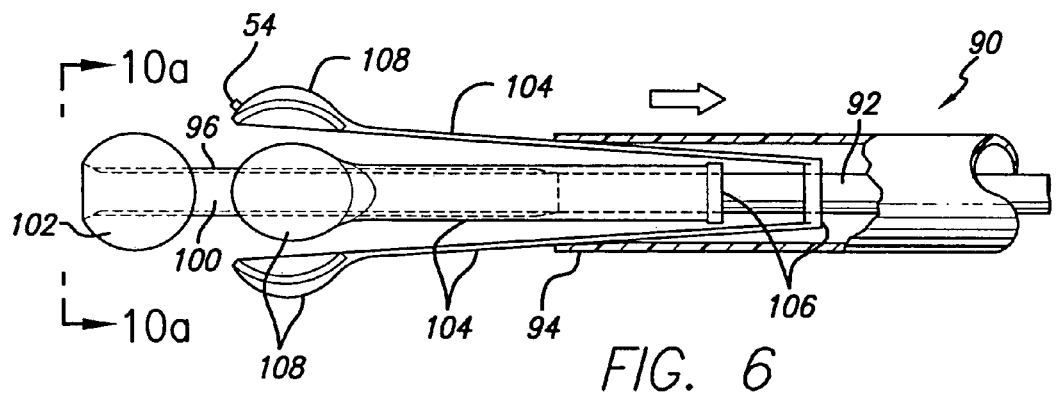
FIG. 6
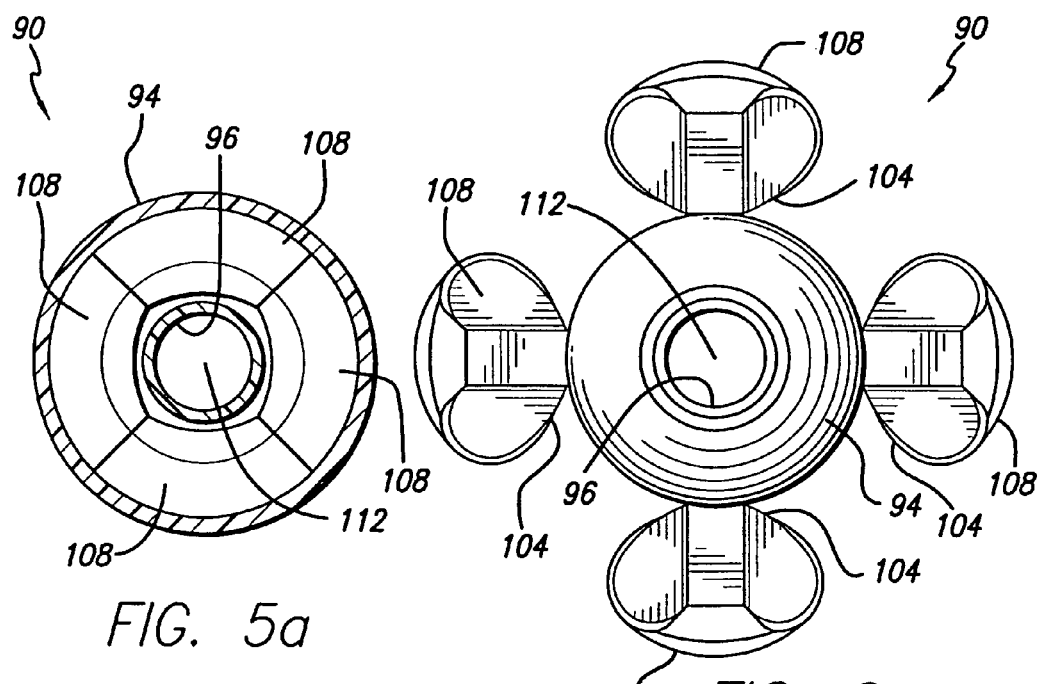
FIG. 5a
FIG. 6a

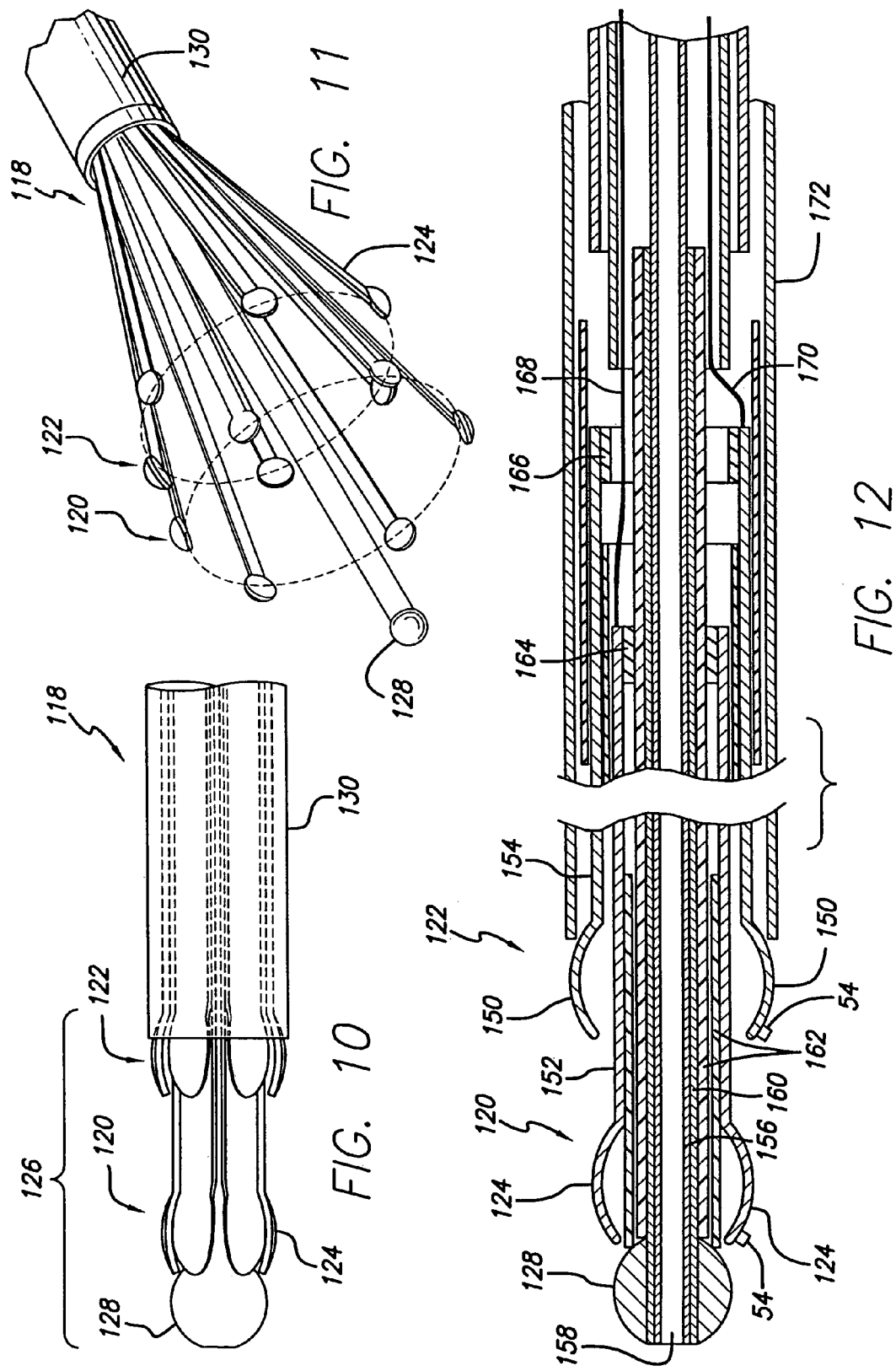

METHOD AND APPARATUS FOR POSITIONING A CATHETER RELATIVE TO AN ANATOMICAL JUNCTION

BACKGROUND

The invention relates generally to a method and apparatus for positioning a catheter relative to a junction in a hollow anatomical structure, such as a vein, including but not limited to, superficial and perforator veins, hemorrhoids, and esophageal varices. The catheter can include an electrode device having multiple leads for applying energy to the anatomical structure to cause it to durably assume a ligated form.

The human venous system of the lower limbs consists essentially of the superficial venous system and the deep venous system with perforating veins connecting the two systems. The superficial system includes the long or great saphenous vein (GSV) and the short saphenous vein. The deep venous system includes the anterior and posterior tibial veins which unite to form the popliteal vein, which in turn becomes the femoral vein (FV) when joined by the short saphenous vein. As illustrated in FIG. 1, The great saphenous vein (GSV) travels through the deep fascia and meets the femoral vein (FV) at the sapheno-femoral junction (SFJ).

The venous system contains numerous one-way valves for directing blood flow back to the heart such as those valves 20 located in the vein 22 shown in FIG. 1. The arrow leading out the top of the vein represents the antegrade flow of blood back to the heart. Venous valves are usually bicuspid valves, with each cusp 24 forming a sack or reservoir 26 for blood which, under retrograde blood pressure, forces the free surfaces of the cusps together to prevent retrograde flow of the blood and allows only antegrade blood flow to the heart. Competent venous valves prevent retrograde flow as blood is pushed forward through the vein lumen and back to the heart. When an incompetent valve 28 is in the flow path, the valve is unable to close because the cusps do not form a proper seal and retrograde flow of the blood cannot be stopped. When a venous valve fails, increased strain and pressure occur within the lower venous sections and overlying tissues, sometimes leading to additional valvular failure. Incompetent valves may result from the stretching of dilated veins. As the valves fail, increased pressure is imposed on the lower veins and the lower valves of the vein, which in turn exacerbates the failure of these lower valves. A cross-sectional perspective view of a dilated vein with an incompetent valve 28 taken along lines 2-2 of FIG. 1 is illustrated in FIG. 2. The valve cusps 24 can experience some separation at the commissure due to the thinning and stretching of the vein wall at the cusps. Two venous 10 conditions which often result from valve failure are varicose veins and more symptomatic chronic venous insufficiency.

The varicose vein condition includes dilation and tortuosity of the superficial veins of the lower limbs, resulting in unsightly discoloration, pain, swelling, and possibly ulceration. Varicose veins often involve incompetence of one or more venous valves, which allow reflux of blood within the superficial system. This can also worsen deep venous reflux and perforator reflux. Current treatments of vein insufficiency include surgical procedures such as vein stripping, ligation, and occasionally, vein-segment transplant.

Chronic venous insufficiency involves an aggravated condition of varicose veins which may be caused by degenerative weakness in the vein valve segment, or by hydrodynamic forces acting on the tissues of the body, such as the legs, ankles, and feet. As the valves in the veins fail, the hydrostatic pressure increases on the next venous valves down, causing those veins to dilate. As this continues, more venous valves will eventually fail. As they fail, the effective height of the column of blood above the feet and ankles grows, and the weight and hydrostatic pressure exerted on the tissues of the ankle and foot increases. When the weight of that column reaches a critical point as a result of the valve failures, ulcerations of the ankle begin to form, which start deep and eventually come to the surface.

Varicose veins can be treated by intra-luminal Ligation. As used herein, "ligation" or "intra-luminal ligation" comprises the occlusion, collapse, or closure of a lumen or hollow anatomical structure by the application of energy from within the lumen or structure. As used herein, "ligation" or "intraluminal ligation" includes electro-ligation. An electrode device is introduced into the lumen and RF energy is applied to the wall by the electrode device to ligate or close off the lumen.

The ligation treatment is often commenced at the saphenofemoral junction (SFJ) in order to close down the tributaries in the region and prevent the subsequent development of alternate flow paths which can lead to recurrent varicosities. Improper placement of the catheter past the SFJ and into the femoral vein could cause heating of the blood or vein walls in the deep venous system.

The location of a catheter within the body of a patient is routinely detected by the use of imaging equipment, such as ultrasound or X-ray equipment. The imaging equipment allows the operator to place the electrode catheter near the SFJ. Such a procedure, however, requires transportation of the patient to an ultrasound or X-ray facility or, conversely, transportation of the ultrasound or X-ray equipment to the patient. Such imaging equipment is bulky, requires an additional person to operate the equipment, and can be time consuming to use. This can be both inconvenient and costly. Physiological factors can also interfere with the resolution of the system and prevent the acquisition of a clean image. Moreover, scheduling difficulties may arise based on the availability of the ultrasound facility or equipment, thereby delaying the minimally invasive treatment which would benefit the patient.

Although described above in terms of a vein, the concepts are generally applicable to other hollow anatomical structures in the body as well. The above description has been generally confined to veins in consideration of avoiding unnecessary repetition.

There is a need in the art for an apparatus and method for determining the location of a catheter near a junction of an anatomical hollow structure within the body of a patient which avoids the need for bulky imaging equipment. The present invention fulfills this and other needs.

SUMMARY OF THE INVENTION

The present invention is directed to a method of positioning a catheter proximate to a junction in a hollow anatomical structure, the method comprising the steps of introducing a catheter into the hollow anatomical structure; identifying the junction in the hollow anatomical structure based on feedback from the catheter without imaging the hollow anatomical structure during the treatment; positioning the working end of the catheter proximate to the location identified in the step of identifying.

In another aspect of the invention, the feedback from the catheter is light emitted from the catheter, wherein the emitted light is visible externally from the patient, and the light disappears as the catheter goes deeper into the anatomy as it nears or enters the anatomical junction.

In another aspect of the invention, the feedback from the catheter is magnetically activated. Where the magnetic feedback system is capable of detecting the orientation of the working end of the catheter, such as by utilizing horizontally-orientated and vertically-orientated magnetic fields generated by a hand-held instrument placed adjacent the patient, the location of the sapheno-femoral junction can be determined from the change in orientation of the working end of the catheter as it dives toward the sapheno-femoral junction. In yet another aspect of the invention, the feedback from the catheter is a radio-frequency signal from a transmitter located at the working end of the catheter. The feedback can also be from an ultrasound transducer or transponder.

In another aspect of the invention, the feedback from the catheter is based on a characteristic measured at the working end of the catheter to determine the flow rate in the vein. The flow rate should increase going from the saphenous vein to the femoral vein at the sapheno-femoral junction. Where the flow rate is determined while the vein is undergoing compression, the compressed saphenous vein would have zero flow (or near zero flow) while the femoral vein would still exhibit some flow since it is deeper in the leg. The working end of the catheter can be momentarily energized, and the subsequent temperature decay can be used to determine the flow rate.

In another aspect of the invention, the feedback from the catheter is mechanically based on a hook-shaped guide wire which engages the ostium of the sapheno-femoral junction.

These and other aspects and advantages of the present invention will become apparent from the following more detailed description, when taken in conjunction with the accompanying drawings which illustrate, by way of example, embodiments of the invention.

BRIEF DESCRIPTION OF THE DRAWINGS

FIG. 5 is a cross-sectional view of the working end of an embodiment of a catheter having a fiber optic device at the working end of the catheter in accordance with the invention;

FIG. 5a is an end-on view of the non-expanded embodiment of FIG. 5;

FIG. 6 is a cross-sectional view of the working end of an embodiment of a hook-shaped guide wire in accordance with the invention;

FIG. 6a is an end-on view of the expanded embodiment of FIG. 6;

FIG. 10 is a side view of the non-expanded tip of an energy application device.

FIG. 11 is a perspective view of an expanded tip of an energy application device.

FIG. 12 is a cross-sectional view of a non-expanded tip of an energy application device.

DETAILED DESCRIPTION OF THE EMBODIMENTS

Figure 1:
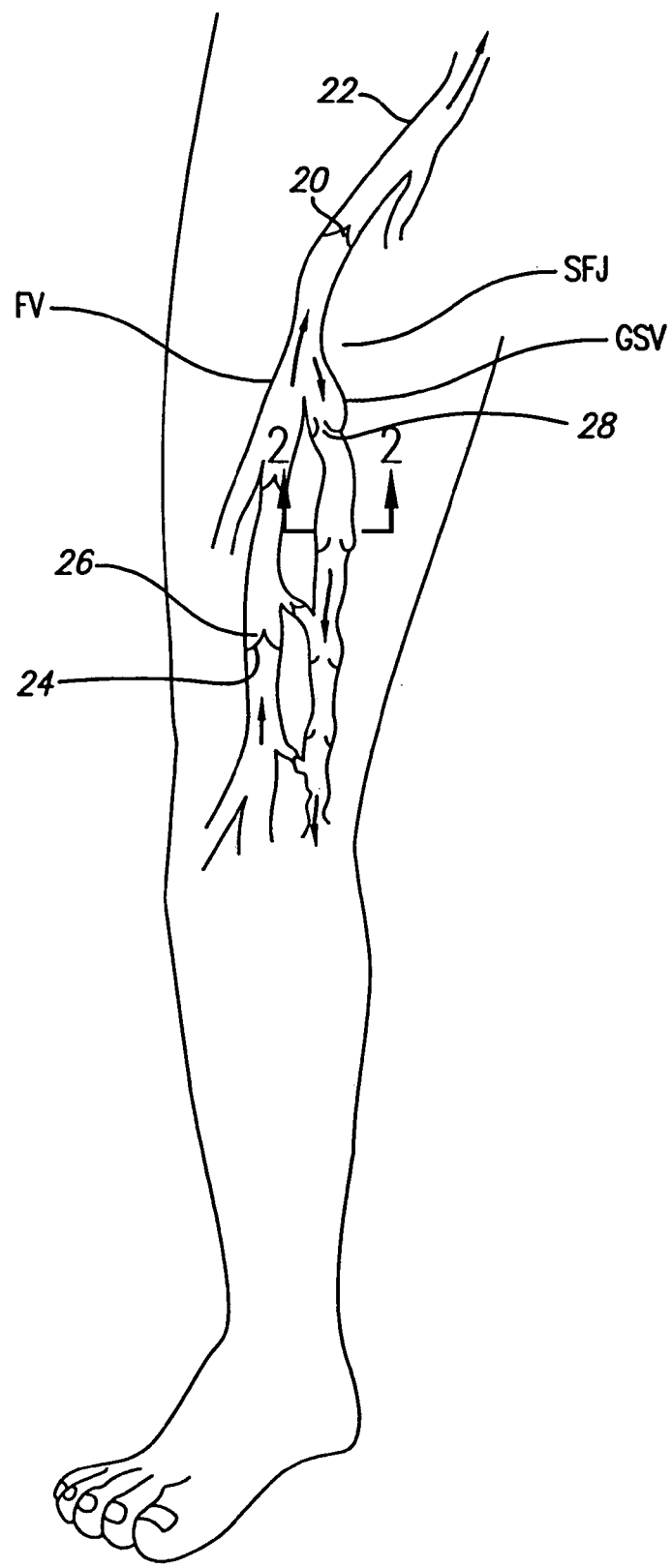
FIG. 1 shows a cross-sectional view of a vein having competent valves and having a dilated section with incompetent venous valves in a lower limb which are to be treated in accordance with the present invention.

As shown in the exemplary drawings, the invention is directed toward the positioning of a catheter to a treatment site for the intravenous treatment of veins. As used herein, like reference numerals will designate similar elements in the various embodiments of the present invention to be discussed. In addition, unless otherwise noted, the term "working end" will refer to the direction toward the treatment site in the patient, and the term "connecting end" will refer to the direction away from the treatment site in the patient. Although the use of RF energy is discussed, it is to be understood that other forms of energy such as microwaves, ultrasound, direct current, circulating heated fluid, radiant light, and lasers can be used, and that the thermal energy generated from a resistive coil or curie point element may be used as well. The invention will be described in relation to the treatment of the venous system of the lower limbs, such as the saphenous vein in the leg. It is to be understood, however, that the invention is not limited thereto and may be employed intraluminally to treat veins in other areas of the body.

Figure 2:
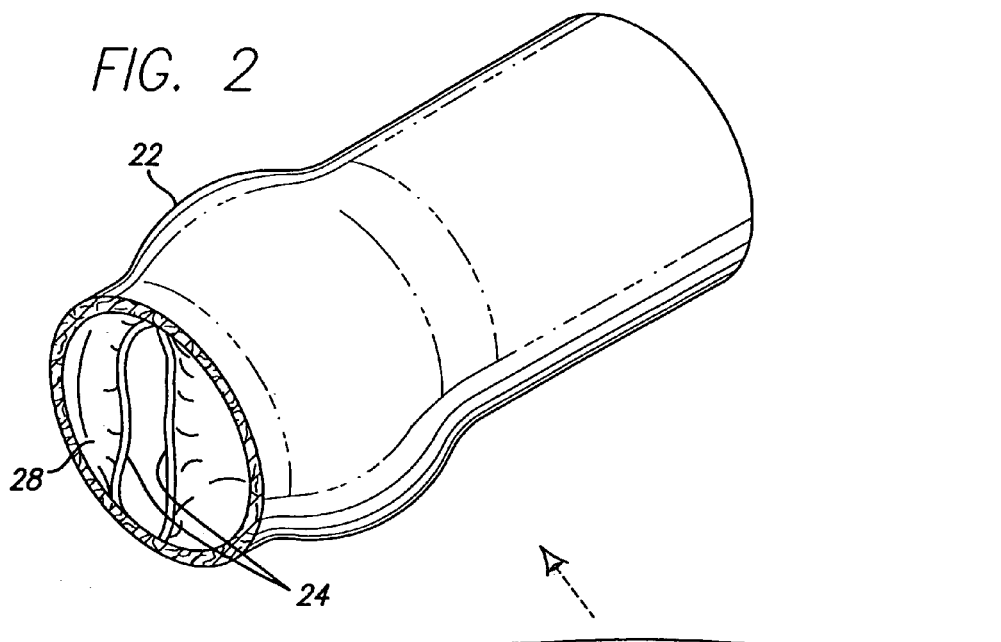
FIG. 2 shows a representative view of a venous section with an incompetent valve from FIG. 1 taken along lines 2-2 which is to be treated in accordance with the present invention.
Figure 4:
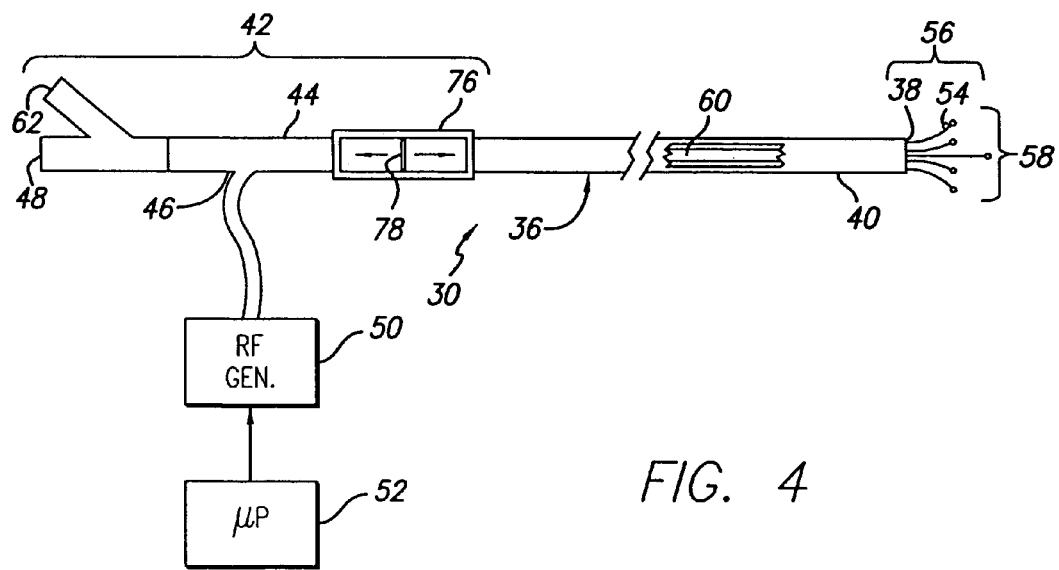
FIG. 4 is a diagram of an energy application system that may be used in conjunction with the method of the present invention, depicting a partial cutaway view of the first embodiment of the catheter showing both the working end and the connecting end with an RF generator and a microprocessor connected at the connection end.

There are many instances in clinical medicine where detecting the location of a catheter within a patient is important, especially in relation to a specific part of the anatomy. For treating varicose veins in the leg, often it is preferable to begin ligating at the sapheno-femoral junction (SFJ) since, as shown in FIG. 1, that is where the highest point of reflux frequently occurs. As shown in FIG. 2, reflux occurs because the valves in the vein fail to close properly. A catheter 30 carrying an electrode device 32, such as that shown in FIG. 4, is introduced into the vein and placed near the sapheno-femoral junction (SFJ). The electrode catheter can be placed intraluminally near the sapheno-femoral junction (SFJ). Either before or after the location of the SFJ has been ascertained, the tissue surrounding the treatment site can be hi compressed via an elastic compression wrap, inflatable cuff, or a tumescent anesthesia technique. The tumescent anesthesia technique is described in copending patent application Ser. No. 09/322,326, which is hereby incorporated by reference in its entirety. The tumescent anesthesia technique involves a dilute anesthetic solution which is injected into the tissue surrounding the vein to be treated. The expandable electrode device which has been introduced into the patient is then expanded into non-penetrating apposition with the venous tissue after compression of the vein. The electrode is then activated, and energy such as high frequency RF energy is applied from the expandable electrode device to the venous tissue until the vein durably assumes dimensions less than or equal to the compressed dimensions. The catheter pulled back to ligate or close off an extensive section of the saphenous vein (GSV).

One embodiment of the catheter 30 includes the expandable electrode device 56 that moves in and out of the outer sheath by way of the distal orifice 38, although in other embodiments the device 56 may expand from and contract into the catheter 30 at other locations. The expandable electrode device 56 includes a plurality of electrodes 58 which can be expanded by moving the outer sheath 36 relative to the electrodes.

An actuator 76 controls the extension of the electrode device 56 through the distal orifice 38. The actuator may take the form of a lever 78, switch, threaded control knob, or other suitable mechanism, and is preferably one that can provide fine control over the movement of the outer sheath 36 or the inner sheath 60, as the case may be. In one embodiment of the invention, the actuator interfaces with the outer sheath to move it back and forth relative to the inner sheath. In another embodiment the actuator interfaces with the inner sheath to move it back and forth relative to the outer sheath.

Operation of the actuator 76 causes relative movement of the outer sheath such that the outer sheath no longer restrains the electrodes, and the primary electrodes 58 are moved by the primary leads move outward relative to the axis defined by the outer sheath, while the central secondary electrode 59 remains substantially linear along the axis defined by the outer sheath. The primary leads continue to move outward until the electrodes are placed in apposition with the vein wall and the outward movement of the primary leads is impeded. The primary electrodes 58 contact the vein wall along a generally circumferential area or band of the vein wall.

When the electrodes 58 are positioned at the treatment site of the vein, the RF generator 50 is activated to provide suitable RF energy to produce a thermal effect which causes the venous tissue to shrink, reducing the diameter of the vein. The primary lead electrodes are pressed closer together by the shrinking vein wall and assume a reduced profile shape which is sufficiently small so that the vein is effectively ligated.

Figure 3:
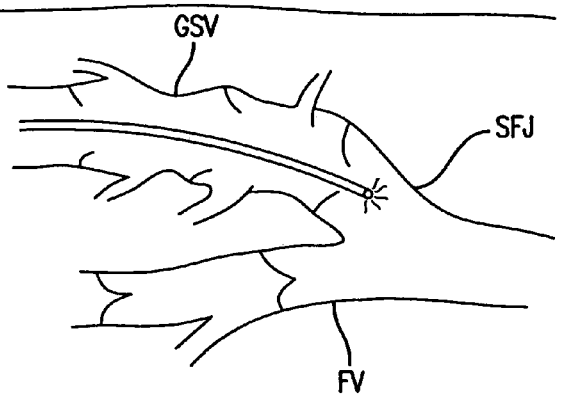
FIG. 3 is a cross-sectional view of a vein and a fiber optic device introduced as delivered to the sapheno-femoral junction.

While ultrasound guidance can be used to determine the location of the sapheno-femoral junction (SFJ) for the procedure, the use of ultrasound imaging equipment can be both costly and inconvenient. Turning to FIG. 3, one method of determining the location of the sapheno-femoral junction (SFJ) involves the use of a fiber optic device 35. The fiber optic device 35 is introduced into the saphenous vein (GSV) through an incision, and directed toward the sapheno-femoral junction (SFJ). The fiber optic device 35 is connected to a light source. The light emitted from the fiber optic device 35 is visible externally from the patient, thereby providing visual feedback to allow the physician to monitor the progress and location of the fiber optic device 35 in the patient. Fiber optic devices often emit light forward in a directional manner. The fiber optic device 35 can be constructed to emit light in a radial fashion to facilitate external visualization.

The saphenous vein (GSV) travels past the deep fascia as it approaches the sapheno-femoral junction (SFJ). The point where the light from the fiberoptic device 35 dims or is no longer visible externally from the patient is marked to identify the location of the sapheno-femoral junction (SFJ) as an anatomical landmark. The length of the fiber optic device 35 that has been introduced into the patient is recorded.

When the fiber optic device 35 is removed from the patient, the catheter 30 is introduced through the same incision for the same length as the fiber optic device that was introduced into the patient. Having traveled the same distance as the fiber optic device 35, the electrode device at the working end of the catheter 30 should be proximate to the sapheno-femoral junction (SFJ).

The electrode device is activated to begin the ligation procedure. Suitable electrode catheters and vein ligation techniques are described in co-pending U.S. patent application Ser. Nos. 08/927,251 and 09/267,127, which are hereby incorporated by reference.

In one embodiment, the catheter 30 includes a lumen which runs substantially along the axis of the inner member before terminating at the guide wire port 48 of the handle 44. In one embodiment, the lumen travels through the central electrode 59. A guide wire can be introduced through the lumen of the catheter for use in guiding the catheter to the desired treatment site. Instead of using a conventional guide wire, the fiber optic device 35 can be utilized as a guide wire, thereby eliminating the need to remove the fiber optic device 35 before the introduction of the catheter 30. The catheter can travel over the fiber optic device to arrive at the desired sapheno-femoral junction (SFJ). The light-emitting portion of the fiber optic device can be configured to emit light in a radial non-directional manner. In another embodiment of the catheter, a fiber optic device is combined as part of the working end of the catheter, and a conventional guide wire can be introduced through the guide wire port and lumen.

The embodiment shown in FIG. 5 is similar to FIG. 4, except that the central electrode 59 has been replaced by an integrated fiber optic device 85 which emits light in a radial fashion. While the integrated fiber optic device 85 does not include a separate lumen for a guide wire, it is to be understood that a lumen may be formed through the fiber optic device 85. As previously discussed, once the fiber optic device travels past the deep fascia layer to near the sapheno-femoral junction (SFJ), the emitted light will dim or no longer be visible externally from the patient. This configuration avoids the need to remove the fiber optic device prior to the introduction of the electrode catheter. This configuration also allows for a more direct determination of the position of the catheter relative to the sapheno-femoral junction (SFJ).

In another method, ultrasound can be used to identify the location of the patient's sapheno-femoral junction (SFJ) prior to the treatment procedure of ligating the vein, but ultrasound imaging need not be used during the procedure. The SFJ is identified by ultrasound prior to the procedure, and the location of the SFJ is externally marked on the skin of the patient. During the procedure, the working end of the catheter is positioned at the externally marked location based on the feedback from the signal detection mechanism in the catheter. For example, an electromagnetic position sensing system, such as that described in U.S. Patent No. 5,645,065, can be utilized. It is to be understood that other signal detection and feedback mechanisms such as ultrasonic transducers or transponders, and radio-frequency transmitters can be used at the working end of the catheter. The signal detection or feedback mechanisms, such as an ultrasonic transducer/transponder or radio-frequency transmitter, can also be used in a separate wire over which the catheter is advanced or introduced. The feedback mechanism can be in the form of a separate wire inserted into a lumen of the catheter, or a sensor integrated into the catheter. The working end of the catheter is positioned at the externally marked location based on the feedback from the signal detection mechanism.

In another embodiment, a magnetic position sensing system is additionally capable of detecting the change in orientation of the working end of the catheter as it dives toward the sapheno-femoral junction (SFJ) to indicate the placement and location of the catheter. The catheter can transmit or receive a signal based on a magnetic field. In one embodiment, a magnet located at the working end of the catheter provides horizontally and vertically generated feedback to the sensing system to indicate position and orientation. An instrument external to the patient monitors the orientation of the working end of the catheter based on the feedback from the magnet. The magnet can be integral to the catheter, or part of a separate wire over which the catheter is introduced or advanced. The magnet can be either passive (static) or active. In another embodiment, the catheter can receive a signal based on a magnetic field generated outside the patient.

One embodiment of the catheter for delivering an expandable energy application device or expandable electrode device 56 to the venous treatment site is illustrated in FIG. 4. The catheter 30 includes an expandable energy application device 56 which in this embodiment, comprises an array of electrodes 58, an outer sheath 36 having a distal orifice 38 at its working end 40. The connector end 42 of the outer sheath is attached to a handle 44 that includes electrical connector 46. The handle additionally includes a guide wire port 48. The connector 46 is for interfacing with a power source, typically an RF generator 50, and a microprocessor controller 52. The microprocessor controller receives data from a sensor 54, such as a thermocouple or impedance sensor, at an intraluminal venous treatment site. Although FIG. 4 illustrates a plurality of electrodes 58 surrounding a single central electrode 59, different electrode configurations may be used.

The sensor 54 also provides data signals for determining the flow rate from the working end of the catheter. The sensor 54 can be a thermocouple to measure the temperature decay after momentarily energizing the electrode to cause a small heating effect. Another embodiment would be to measure the power required to maintain the electrode at a constant temperature. The required power to maintain a constant temperature would increase as the flow increases. In another embodiment, the temperature rise for a fixed input power can be measured. The temperature rise for a fixed input power will decrease as flow increases.

With the saphenous vein under compression, the flow rate should increase going from the saphenous vein to the femoral vein at the sapheno-femoral junction. The compressed saphenous vein would have zero to near zero flow while the femoral vein would still exhibit some flow since it is deeper.

Another method of measuring flow rate employs a flow wire which can be used prior to the introduction of the catheter, or through the central lumen of the catheter, to determine the flow rate in the vein.

The sensor 54 can be an impedance sensor to measure the impedance of the surrounding anatomy at the working end of the catheter. Impedance measurements can also be used to direct and confirm the specific placement of the catheter at the ostium of a vessel such as the SFJ. The impedance will be low when the electrodes are in the blood stream. A higher impedance value indicates electrode contact with the vein wall.

FIG. 6 illustrates a catheter where a hook-shaped guide wire 87 is placed through the central lumen 80. The hook-shaped guide wire 87 can have a hook-shaped tip, or be formed from a shape-memory metal so that the tip would become hook-shaped at a specific temperature, or be fabricated with a flexible tip that could be shaped into a hook pulling on a wire attached eccentrically to the flexible tip. The hook-shaped tip would mechanically engage the ostium of the sapheno-femoral junction (SFJ).

Once the tip of the guide wire 87 is mechanically hooked to the SFJ, the catheter can be positioned relative to the SFJ. In one method, the length of the catheter to be introduced would be determined by the length of the guide wire remaining in the target vessel once the guide wire is engaged with the SFJ.

Figure 7:
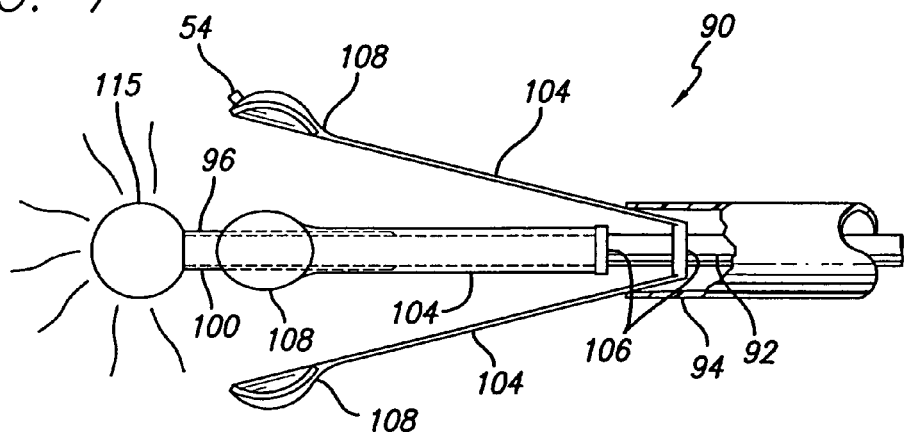
FIG. 7 is a cross-sectional view of the working end of another embodiment of a hook-shaped guide wire in accordance with the invention.

In another method of positioning a catheter relative to the SFJ, illustrated in FIG. 7, a mechanical stop is located proximal to the hook-shaped tip of the guide wire. The mechanical stop can take the form of a sphere, raised bump, or sleeve. As the catheter is introduced over the guide wire, the tip of the catheter encounters the mechanical stop which prevents further insertion over the guide wire. The distance from the mechanical stop to the hook feature positions the catheter tip the desired distance from the SFJ.

Figure 8:
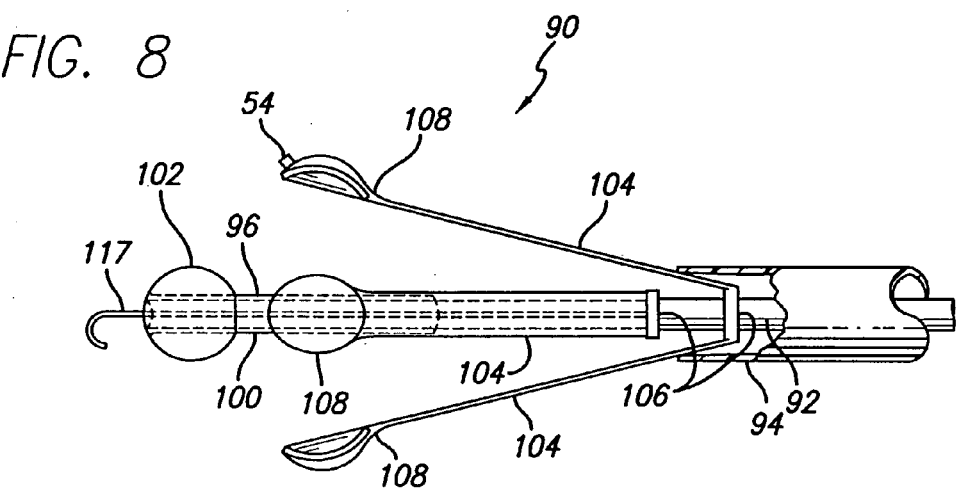
FIG. 8 is a cross-sectional view of the working end of an embodiment of a catheter having a hook-shaped tip in accordance with the invention.
Figure 9:
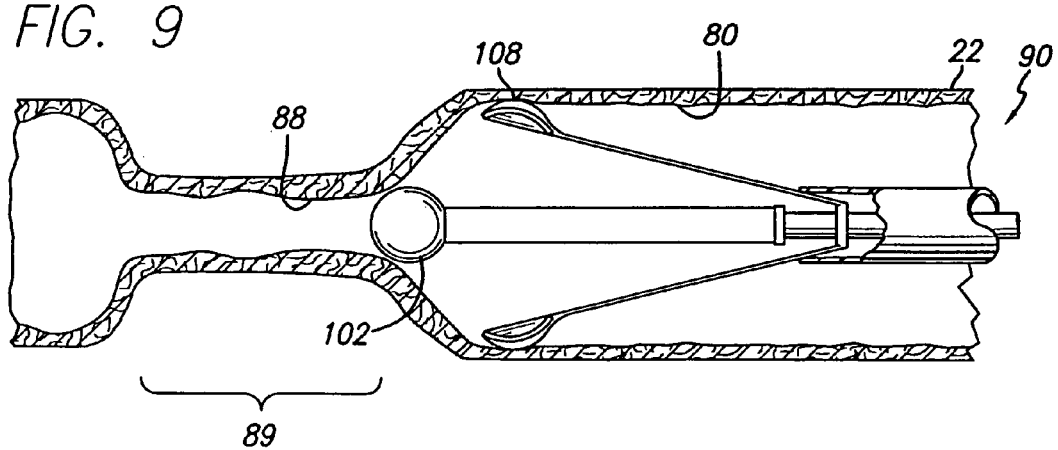
FIG. 9 is a cross-sectional view showing an expandable energy application device within a hollow anatomical structure.

In the embodiment illustrated in FIG. 8, the catheter itself includes a hook-shaped tip. The hook-shaped tip can be made integral to the catheter. The tip can be preformed into a hook shape, or fabricated from a shape memory metal so that the tip would assume a hook shape at a specific temperature, or be fabricated from a flexible material that could be shaped into a hook pulling on a wire attached eccentrically to the flexible tip. To activate the hook shape, the handle of the catheter would include a device to cause the heating of the shape memory metal embodiment. In another embodiment, the handle would include a mechanism for pulling on a tip-deflecting wire attached at the catheter tip. The hook-shaped tip of the catheter would mechanically engage the ostium of the SFJ and position the catheter electrodes relative to the SFJ before the initial activation of the electrodes. Prior to pulling back on the catheter to collapse a length of the vein or vessel, the hook-shaped tip is straightened to release the catheter from the ostium of the SFJ.

It is to be understood that the catheter can include one or more sensors, such as thermocouples, mounted in place on an electrode so that the sensor is substantially flush with the exposed surface of the electrode. The sensors are shown in a raised position in the drawings for clarity of illustration only. The sensors can be used in conjunction with the fiber optic device or the hook-shaped guide wire to properly position the catheter at the SFJ.

Although described above in terms of a vein, the concepts are generally applicable to other hollow anatomical structures in the body as well. The above description has been generally confined to veins in consideration of avoiding unnecessary repetition.

While several particular forms of the invention have been illustrated and described, it will be apparent that various modifications can be made without departing from the spirit and scope of the invention. Accordingly, it is not intended that the invention be limited, except as by the claims.

What is claimed is:

1. A method of intraluminally positioning an elongate treatment device proximate to a junction in a hollow anatomical structure comprising veins of a patient, the method comprising the steps of:

introducing the treatment device into the hollow anatomical structure, the treatment device comprising an elongate shaft and an electrically driven energy application device at a working end of the shaft;

identifying the junction where two veins intersect in the hollow anatomical structure by emitting light via a fiber optic device positioned in the hollow anatomical structure;

positioning the working end of the treatment device proximate the junction identified in the step of identifying;

applying energy to one of the veins in the hollow anatomical structure proximate the junction via the energy application device so as to reduce the diameter of that vein in the hollow anatomical structure.

2. The method of claim 1 wherein the junction in the step of identifying is the sapheno-femoral junction.

3. The method of claim 1 wherein an attribute of the light changes upon the fiber optic device reaching the junction of the hollow anatomical structure.

4. The method of claim 3 further including the step of measuring the length of the fiber optic device introduced into the patient until the attribute of the light changes.

5. The method of claim 4 further including the step of removing the fiber optic device after the step of measuring.

6. The method of claim 4 wherein the step of positioning further includes the step of inserting the treatment device for the same length as measured in the step of measuring the length of the fiber optic device.

7. The method of claim 1 wherein the step of introducing the treatment device further includes the step of introducing the treatment device over the fiber optic device.

8. The method of claim 1 wherein introducing said treatment device comprises introducing said treatment device over a guidewire with a hook shaped tip located at the distal end of a guide wire, and the hook shaped tip is adaptable to engage the junction of the hollow anatomical structure while the treatment device travels over the guidewire to the junction.

9. The method of claim 1 wherein the step of introducing the treatment device further includes the step of introducing the treatment device over a guide wire.

10. The method of claim 1 wherein the step of applying energy heats but does not cut the vein, and wherein the reduced diameter of the vein results in occlusion of the vein.

11. The method of claim 1, wherein applying energy to one of the veins in the hollow anatomical structure effectively ligates that vein.

12. The method of claim 1 wherein the reduced diameter of the vein results in occlusion of the vein.

13. The method of claim 1, wherein the energy application device comprises a plurality of electrodes.

14. The method of claim 1, wherein the energy application device comprises a resistive coil.

15. The method of claim 1, wherein the fiber optic device is an integrated part of the treatment device.

16. A method of positioning a catheter within a hollow anatomical structure, the method comprising the steps of:
   introducing a guide wire having a hook-shaped tip into the hollow anatomical structure;
   hooking the hook-shaped tip of the guide wire to an ostium of a junction within the hollow anatomical structure;
   introducing a catheter having a working end into the hollow anatomical structure over the guide wire;
   positioning the working end of the catheter proximate the junction identified in the step of hooking; and
   applying energy to the hollow anatomical structure at the treatment site via an energy application device at the working end of the catheter to heat but not cut the hollow anatomical structure until the hollow anatomical structure durably assumes a smaller size such that the reduced diameter of the hollow anatomical structure effectively ligates the hollow anatomical structure.

17. The method of claim 16 wherein the junction in the step of hooking is the sapheno-femoral junction.

18. The method of claim 16 wherein the step of positioning further includes the step of stopping the advancement of the catheter by a mechanical stop located proximal to the hook shaped tip of the guide wire.

19. The method of claim 16 further comprising the step of measuring the length of the guide wire introduced into the patient in the step of hooking.

20. A method of positioning a device for intraluminal application of therapeutic energy to a target portion of a hollow anatomical structure, the method comprising:
   emitting light from a light source within a hollow anatomical structure having first and second lumina;
   monitoring the light from outside the hollow anatomical structure to determine information about the location of a junction between a target portion and a nontarget portion of the hollow anatomical structure;
   introducing a catheter having a working end into the first lumen of the hollow anatomical structure, the catheter having a therapeutic energy device at the working end, the therapeutic energy device being distinct from the light source;
   using the information to position the therapeutic energy device in the target portion in the first lumen near the junction; and
   applying energy from the therapeutic energy device to the target portion in the first lumen of the hollow anatomical structure, thereby shrinking the target portion of the hollow anatomical structure.

21. The method of claim 20, wherein the therapeutic energy device is positioned separately from the light source.

22. The method of claim 20, further comprising the step of expanding the therapeutic energy device to provide physical engagement with the hollow anatomical structure.

23. The method of claim 22, wherein the step of expanding occurs after the step of using the information to position the therapeutic energy device.

24. The method of claim 20, wherein the hollow anatomical structure comprises a blood vessel.

25. The method of claim 20, wherein the hollow anatomical structure is the great saphenous vein, the sapheno-femoral junction, and the femoral vein.

26. The method of claim 20, wherein the target portion is the great saphenous vein.

27. The method of claim 20, wherein the light source is a fiber optic device.

28. The method of claim 27, wherein the fiber optic device is configured to emit light in a radial fashion.

29. The method of claim 20, wherein the therapeutic energy device is an electrode device.

30. The method of claim 20, wherein the catheter includes the light source.

31. The method of claim 30, wherein the light source is combined as part of the working end of the catheter.

32. The method of claim 20, wherein the therapeutic energy device is a resistive coil.

33. A method of positioning a device for application of therapeutic energy to a target portion of a system of two blood vessels, the method comprising:
   emitting visual feedback light from a visual feedback device positioned within the system of two blood vessels;
   monitoring the visual feedback light from outside the system of two blood vessels to determine information about the location of a junction between a target portion and a non-target portion of the system of two blood vessels;
   introducing, into the first vessel, a catheter having a therapeutic energy device at the catheter's working end, the therapeutic energy device distinct from the visual feedback device;
   using the information to position the therapeutic energy device near the junction and prevent the therapeutic energy device from extending into the non-target portion; and
   shrinking the target portion of the system of two blood vessels by applying energy from the therapeutic energy device to the target portion.

34. The method of claim 33, wherein therapeutic energy device is positioned separately from the visual feedback device.

35. The method of claim 33, wherein the target portion is in the saphenous vein.

36. The method of claim 33, wherein the non-target portion is the femoral vein.

37. The method of claim 33, wherein the visual feedback device is configured to emit light in a radial fashion.

38. The method of claim 33, wherein the catheter comprises the visual feedback device.

39. The method of claim 33, wherein the therapeutic energy device comprises a resistive coil.

\* \* \* \* \*

UNITED STATES PATENT AND TRADEMARK OFFICE
CERTIFICATE OF CORRECTION

PATENT NO. : 7,789,876 B2
APPLICATION NO. : 09/825741
DATED : September 7, 2010
INVENTOR(S) : Arthur W. Zikorus et al.

It is certified that error appears in the above-identified patent and that said Letters Patent is hereby corrected as shown below:

Title page 1, Item (75) Inventors, delete "Walnut Creek, CA" and insert -- Washington, D.C. --, therefore.

Title page 1, under Item (65), insert heading -- Related U.S. Application Data --.

Title page 1, under Item (65) and the heading inserted above, insert -- Continuation of application No. 09/638,307, filed on Aug. 14, 2000, now abandoned. --.

Title page 1, item (57), line 10 of the ABSTRACT, after "may no longer" insert -- be --.

At column 1, line 50, after "venous" delete "10".

At column 4, line 46, after "site can be" delete "hi".

At column 5, line 60 (Approx.), after "the working end of" delete "20".

Signed and Sealed this
Twenty-eighth Day of December, 2010

David J. Kappos
*Director of the United States Patent and Trademark Office*